(12) United States Patent
Middleton et al.

(10) Patent No.: US 8,845,603 B2
(45) Date of Patent: Sep. 30, 2014

(54) SILENCER FOR VACUUM SYSTEM OF A WOUND DRAINAGE APPARATUS

(75) Inventors: Max Middleton, London (GB); Stephen Jacob, Cambridgeshire (GB)

(73) Assignee: Smith & Nephew PLC, London (GB)

( * ) Notice: Subject to any disclaimer, the term of this patent is extended or adjusted under 35 U.S.C. 154(b) by 772 days.

(21) Appl. No.: 12/667,375

(22) PCT Filed: Jun. 27, 2008

(86) PCT No.: PCT/GB2008/050509
§ 371 (c)(1),
(2), (4) Date: Dec. 30, 2009

(87) PCT Pub. No.: WO2009/004369
PCT Pub. Date: Jan. 8, 2009

(65) Prior Publication Data
US 2010/0185165 A1    Jul. 22, 2010

(30) Foreign Application Priority Data
Jul. 2, 2007    (GB) .................................. 0712739.2

(51) Int. Cl.
*A61M 1/00* (2006.01)
*A61M 27/00* (2006.01)

(52) U.S. Cl.
CPC ..... *A61M 1/0066* (2013.01); *A61M 2205/3379* (2013.01); *A61M 1/0031* (2013.01); *A61M 1/0052* (2014.02); *A61M 2205/3331* (2013.01); *A61M 2205/18* (2013.01); *A61M 2205/3365* (2013.01); *A61M 2205/75* (2013.01); *A61M 1/0027* (2014.02); *A61M 2205/8206* (2013.01); *A61M 2205/8262* (2013.01); *A61M 1/0029* (2014.02); *A61M 27/00* (2013.01); *A61M 1/0088* (2013.01); *A61M 2205/42* (2013.01); *A61M 1/0096* (2014.02); *A61M 2205/502* (2013.01)
USPC .......................................... 604/317; 604/543

(58) Field of Classification Search
USPC ................... 604/317–327, 540–543
See application file for complete search history.

(56) References Cited

U.S. PATENT DOCUMENTS

| 4,382,441 A | 5/1983 | Svedman |
| 4,634,061 A | 1/1987 | Williams |

(Continued)

FOREIGN PATENT DOCUMENTS

| DE | 39 35 818 A1 | 5/1991 |
| EP | 0669463 | 8/1995 |

(Continued)

OTHER PUBLICATIONS

U.S. Appl. No. 12/667,228, filed Dec. 29, 2009, Jake Turner et al.

(Continued)

*Primary Examiner* — Philip R Wiest
*Assistant Examiner* — Benjamin Klein
(74) *Attorney, Agent, or Firm* — Knobbe, Martens, Olson & Bear, LLP

(57) ABSTRACT

Apparatus (10, 200) for the provision of TNP therapy to a wound is described, the apparatus (10, 200) including: a waste canister (22, 204) into which fluid is aspirated from a wound by aspiration pump means (44, 248) and a fluid flow path (420, 422) for at least a part of said aspirated fluid on an outlet side of said aspiration pump means (44) wherein said fluid flow path (420, 422) on the outlet side comprises a silencing system (400) having a plurality of silencing elements (402, 404, 406) therein.

18 Claims, 10 Drawing Sheets

(56) References Cited

U.S. PATENT DOCUMENTS

| | | | |
|---|---|---|---|
| 4,767,417 A | 8/1988 | Boehringer | |
| 4,826,513 A | 5/1989 | Stackhouse | |
| 4,963,134 A | 10/1990 | Backscheider | |
| 4,969,880 A | 11/1990 | Zamierowski | |
| 5,176,663 A | 1/1993 | Svedman | |
| 5,358,494 A | 10/1994 | Svedman | |
| 5,391,060 A * | 2/1995 | Kozumplik et al. | 417/393 |
| 5,466,229 A * | 11/1995 | Elson et al. | 604/317 |
| 5,527,293 A | 6/1996 | Zamierowski | |
| 5,636,643 A | 6/1997 | Argenta | |
| 5,645,081 A | 7/1997 | Argenta | |
| 5,738,656 A | 4/1998 | Wagner | |
| 5,894,608 A * | 4/1999 | Birbara | 4/144.3 |
| 6,071,267 A | 6/2000 | Zamierowski | |
| 6,117,111 A | 9/2000 | Fleischmann | |
| 6,142,982 A | 11/2000 | Hunt | |
| 6,368,311 B1 | 4/2002 | Valerio | |
| 6,398,767 B1 | 6/2002 | Fleischmann | |
| 6,458,109 B1 | 10/2002 | Henley | |
| 6,648,862 B2 | 11/2003 | Watson | |
| 6,752,794 B2 | 6/2004 | Lockwood | |
| 6,755,807 B2 | 6/2004 | Risk, Jr. | |
| 6,764,462 B2 | 7/2004 | Risk, Jr. | |
| 6,800,074 B2 | 10/2004 | Henley | |
| 6,824,533 B2 | 11/2004 | Risk, Jr. | |
| 6,935,459 B2 | 8/2005 | Austin et al. | |
| 6,936,037 B2 | 8/2005 | Bubb | |
| 7,004,915 B2 | 2/2006 | Boynton | |
| 7,022,113 B2 | 4/2006 | Lockwood | |
| 7,077,832 B2 | 7/2006 | Fleischmann | |
| 7,108,683 B2 | 9/2006 | Zamierowski | |
| 7,195,624 B2 | 3/2007 | Lockwood | |
| 7,198,046 B1 | 4/2007 | Argenta | |
| 7,216,651 B2 | 5/2007 | Argenta | |
| 7,276,051 B1 * | 10/2007 | Henley et al. | 604/304 |
| 7,381,859 B2 | 6/2008 | Hunt et al. | |
| 7,438,705 B2 | 10/2008 | Karpowicz | |
| 7,524,315 B2 | 4/2009 | Blott | |
| 7,534,240 B1 | 5/2009 | Johnson | |
| 7,534,927 B2 | 5/2009 | Lockwood et al. | |
| 7,553,306 B1 | 6/2009 | Hunt et al. | |
| 7,608,066 B2 | 10/2009 | Vogel | |
| 7,625,362 B2 | 12/2009 | Boehringer | |
| 7,678,090 B2 | 3/2010 | Risk, Jr. | |
| 7,794,450 B2 | 9/2010 | Blott et al. | |
| 7,818,835 B2 | 10/2010 | Heaton et al. | |
| 7,837,673 B2 | 11/2010 | Vogel | |
| 7,857,806 B2 * | 12/2010 | Karpowicz et al. | 604/540 |
| 8,162,909 B2 * | 4/2012 | Blott et al. | 604/319 |
| 2002/0198503 A1 | 12/2002 | Risk, Jr. | |
| 2003/0050594 A1 | 3/2003 | Zamierowski | |
| 2004/0163884 A1 | 8/2004 | Austin | |
| 2005/0177190 A1 | 8/2005 | Zamierowski | |
| 2007/0016152 A1 | 1/2007 | Karpowicz et al. | |
| 2007/0021697 A1 | 1/2007 | Ginther | |
| 2007/0038172 A1 | 2/2007 | Zamierowski | |
| 2007/0065303 A1 * | 3/2007 | Tomell et al. | 417/312 |
| 2007/0219532 A1 | 9/2007 | Karpowicz et al. | |
| 2007/0240404 A1 * | 10/2007 | Pekrul et al. | 60/282 |
| 2007/0265586 A1 | 11/2007 | Joshi | |
| 2008/0200905 A1 | 8/2008 | Heaton | |
| 2009/0054855 A1 | 2/2009 | Blott et al. | |
| 2009/0069761 A1 | 3/2009 | Vogel | |
| 2009/0254066 A1 | 10/2009 | Heaton | |
| 2009/0270820 A1 | 10/2009 | Johnson | |
| 2009/0326488 A1 * | 12/2009 | Budig et al. | 604/319 |
| 2010/0063483 A1 | 3/2010 | Adahan | |
| 2010/0106112 A1 | 4/2010 | Vogel | |
| 2010/0278518 A1 | 11/2010 | Gordon | |
| 2010/0312202 A1 * | 12/2010 | Henley et al. | 604/319 |
| 2011/0028921 A1 | 2/2011 | Hartwell et al. | |
| 2011/0071483 A1 | 3/2011 | Gordon et al. | |

FOREIGN PATENT DOCUMENTS

| | | |
|---|---|---|
| EP | 0777504 B1 | 10/1998 |
| EP | 0688189 | 9/2000 |
| EP | 1440667 | 7/2004 |
| EP | 1171065 | 3/2007 |
| GB | 2195255 A4 | 4/1988 |
| GB | 2307180 A | 5/1997 |
| SU | 1251912 A1 | 4/1983 |
| WO | WO 90/11795 | 10/1990 |
| WO | WO 91/00718 | 1/1991 |
| WO | WO 92/20299 | 11/1992 |
| WO | WO 03/030966 | 4/2003 |
| WO | WO 03/101508 | 12/2003 |
| WO | WO 2006/052745 | 5/2006 |
| WO | WO 2006/135934 A2 | 12/2006 |
| WO | WO 2007/019038 | 2/2007 |
| WO | WO 2007/070570 | 6/2007 |
| WO | WO 2007/070570 A | 6/2007 |
| WO | WO 2007/088530 | 8/2007 |
| WO | WO 2008/030872 A1 | 3/2008 |
| WO | WO 2009/004291 A3 | 1/2009 |
| WO | WO 2009/004367 A1 | 1/2009 |
| WO | WO 2009/019419 | 2/2009 |
| WO | WO 2009/019496 | 2/2009 |

OTHER PUBLICATIONS

U.S. Appl. No. 12/667,231, filed Dec. 29, 2009, Benjamin Gordon et al.

Eurpoean Patent Office; International Search Report of PCT Application, Application No. PCT/GB2008/050509, filed Jun. 27, 2008.

Bagautdinov, N.A., "Variant of External Vacuum Aspiration in the Treatment of Purulent Diseases of Soft Tissues," in current Problems in Modern Clinical Surgery: Interdepartmental Collection, edited by V. Ye. Volkov et al. (Chuvashia State University, Cheboksary, USSR 1986) pp. 94-96.

Karev, I.D., et al., "Foam Drainage System for Treating Purulent Wounds," in Second All-Union Conference "Wounds and Wound Infections" (Presentation Abstracts) (Moscow, USSR 1986) pp. 87-88.

Kuznetsov, V.A. Bagautdinov, N.A., "Vacuum and Vacuum-Sorption Treatment of Open Septic Wounds," in Second All-Union Conference "Wounds and Wound Infections" (Presentation Abstracts) (Moscow, USSR 1986) pp. 91-21.

Chariker, M.E. et al. "Effective Management of Incisional and Cutaneous Fistulae with Close Suction Wound Drainage" *Contemporary Surgery* 1989 34:59-63.

Jeter, K. "Managing Draining wounds and Fistulae: New and Established Methods" Chronic Wound Care pp. 240-246.

Solovev, V. A., et al., "The Method of Treatment of Immature External Fistulas in the Upper Gastrointestinal Tract—Guidelines" USSR Ministry of Health, S. M. Kirov Gorky State Medical Institute, 1987.

Solovev, V.A., "Treatment and Prevention of Suture Failures after Gastric Resection" (Dissertation Abstract) (S.M. Kirov Gorky State Medical Institute, Gorky USSR 1988).

Svedman, P. "A Dressing Allowing Continuous Treatment of a Biosurface" *IRCS Med. Science: Biomed. Tech.; Clinic. Med.,Surg. and Transplantation* 1979 7:221.

Svedman, P. "Irrigation of Treatment of Leg Ulcers" *The Lancet* 1983 pp. 532-534.

Svedman, P. "Irrigation Treatment in Split-Thickness Skin Grafting of Intractable Leg Ulcers" *Scand. J. Plast. Reconst. Surg.* 1985 19:211-213.

Svedman, P. et al. "A Dressing System Providing Fluid Supply and Suction Drainage Used for Continuous or Intermittent Irrigation" *Annals of Plastic Surgery* 1986 17(2):125-133.

International Search Report from Application No. PCT/GB2008/050507 mailed Oct. 15, 2008 in 6 pages.

International Search Report for Application No. PCT/GB2008/050509 mailed Oct. 27, 2008 in 5 pages.

(56) References Cited

OTHER PUBLICATIONS

Levine et al, Implementing the new CMS guidelines for wound care, 2006.

KCI, Info V.A.C. User Manual, Dec. 2006.

International Preliminary Report on Patentability received in PCT/GB2008/050509 mailed on Jan. 5, 2010 in 7 pages.

Communication pursuant to Article 94(3) EPC dated Jul. 6, 2012 received in Application No. EP 08 762 611.5 in 6 pages.

Patent Examination Report No. 1 dated Oct. 31, 2012 received in Application No. 2008272680 in 4 pages.

* cited by examiner

SILENCER FOR VACUUM SYSTEM OF A WOUND DRAINAGE APPARATUS

CROSS-REFERENCE TO RELATED APPLICATIONS

This Application is a U.S. National Phase of the International Application No. PCT/GB2008/050509 filed Jun. 27, 2008 designating the U.S. and published on Jan. 8, 2009 as WO 2009/004369, which claims priority of Great Britain Patent Application No. 0712739.2 filed Jul. 2, 2007.

BACKGROUND OF THE INVENTION

1. Field of the Invention

The present invention relates to apparatus and a method for the application of topical negative pressure (TNP) therapy to wounds. In particular, but not exclusively, the present invention relates to minimising noise generated by TNP therapy apparatus.

2. Background of the Invention

There is much prior art available relating to the provision of apparatus and methods of use thereof for the application of TNP therapy to wounds together with other therapeutic processes intended to enhance the effects of the TNP therapy. Examples of such prior art include those listed and briefly described below.

TNP therapy assists in the closure and healing of wounds by reducing tissue oedema; encouraging blood flow and granulation of tissue; removing excess exudates and may reduce bacterial load and thus, infection to the wound. Furthermore, TNP therapy permits less outside disturbance of the wound and promotes more rapid healing.

In our co-pending International patent application, WO 2004/037334, apparatus, a wound dressing and a method for aspirating, irrigating and cleansing wounds are described. In very general terms, this invention describes the treatment of a wound by the application of topical negative pressure (TNP) therapy for aspirating the wound together with the further provision of additional fluid for irrigating and/or cleansing the wound, which fluid, comprising both wound exudates and irrigation fluid, is then drawn off by the aspiration means and circulated through means for separating the beneficial materials therein from deleterious materials. The materials which are beneficial to wound healing are recirculated through the wound dressing and those materials deleterious to wound healing are discarded to a waste collection bag or vessel.

In our co-pending International patent application, WO 2005/04670, apparatus, a wound dressing and a method for cleansing a wound using aspiration, irrigation and cleansing wounds are described. Again, in very general terms, the invention described in this document utilises similar apparatus to that in WO 2004/037334 with regard to the aspiration, irrigation and cleansing of the wound, however, it further includes the important additional step of providing heating means to control the temperature of that beneficial material being returned to the wound site/dressing so that it is at an optimum temperature, for example, to have the most efficacious therapeutic effect on the wound. In our co-pending International patent application, WO 2005/105180, apparatus and a method for the aspiration, irrigation and/or cleansing of wounds are described. Again, in very general terms, this document describes similar apparatus to the two previously mentioned documents hereinabove but with the additional step of providing means for the supply and application of physiologically active agents to the wound site/dressing to promote wound healing.

The content of the above references is included herein by reference.

However, the above apparatus and methods are generally only applicable to a patient when hospitalised as the apparatus is complex, needing people having specialist knowledge in how to operate and maintain the apparatus, and also relatively heavy and bulky, not being adapted for easy mobility outside of a hospital environment by a patient, for example.

Some patients having relatively less severe wounds which do not require continuous hospitalisation, for example, but whom nevertheless would benefit from the prolonged application of TNP therapy, could be treated at home or at work subject to the availability of an easily portable and maintainable TNP therapy apparatus.

GB-A-2 307 180 describes a portable TNP therapy unit which may be carried by a patient clipped to belt or harness.

Such commercial apparatus are known to be noisy, partly in the interests of keeping weight to a minimum in portable apparatus. However, airborne noise generated from diaphragm pumps, which are often used, is known to be a significant source of irritation and discomfort to the user or patient and also to people in the vicinity. However, many different types of pump may be used including piston pumps, rotary vane pumps, turbo fan, for example, all generate noise. The level of discomfort produced by airborne noise in such apparatus is not to be underestimated as it has been known for patients to turn the apparatus off to alleviate the discomfort with the consequent obvious disadvantages to wound healing. Such commercial apparatus generally employ only a single element silencing comprising a simple cavity having a sound absorbent material therein.

SUMMARY OF SOME EXEMPLIFYING EMBODIMENTS

It is an aim of the present invention to at least partly mitigate the above-mentioned problems.

It is an aim of embodiments of the present invention to provide portable apparatus for providing TNP therapy which is less noisy and produces less discomfort to a patient than known commercial apparatus.

According to a first aspect of the present invention there is provided portable apparatus for the provision of TNP therapy to a wound, the apparatus includes: a waste canister into which fluid is aspirated from a wound by aspiration pump means and a fluid flow path for at least a part of said aspirated fluid on an outlet side of said aspiration pump means wherein said fluid flow path on the outlet side comprises a silencing system having a plurality of silencing elements therein.

The invention is comprised in part of an overall apparatus for the provision of TNP therapy to a patient in almost any environment. The apparatus is lightweight, may be mains or battery powered by a rechargeable battery pack contained within a device (henceforth, the term "device" is used to connote a unit which may contain all of the control, power supply, power supply recharging, electronic indicator means and means for initiating and sustaining aspiration functions to a wound and any further necessary functions of a similar nature). When outside the home, for example, the apparatus may provide for an extended period of operation on battery power and in the home, for example, the device may be connected to the mains by a charger unit whilst still being used and operated by the patient.

The overall apparatus of which the present invention is a part comprises: a dressing covering the wound and sealing at least an open end of an aspiration conduit to a cavity formed over the wound by the dressing; an aspiration tube comprising at least one lumen therethrough leading from the wound dressing to a waste material canister for collecting and holding wound exudates/waste material prior to disposal; and, a power, control and aspiration initiating and sustaining device associated with the waste canister.

The dressing covering the wound may be any type of dressing normally employed with TNP therapy and, in very general terms, may comprise, for example, a semi-permeable, flexible, self-adhesive drape material, as is known in the dressings art, to cover the wound and seal with surrounding sound tissue to create a sealed cavity or void over the wound. There may aptly be a porous barrier and support member in the cavity between the wound bed and the covering material to enable an even vacuum distribution to be achieved over the area of the wound. The porous barrier and support member being, for example, a gauze, foam, inflatable bladder or known wound contact type material resistant to crushing under the levels of vacuum created and which permits transfer of wound exudates across the wound area to the aspiration conduit sealed to the flexible cover drape over the wound.

The aspiration conduit may be a plain flexible tube, for example, having a single lumen therethrough and made from a plastics material compatible with raw tissue, for example. However, the aspiration conduit may have a plurality of lumens therethrough to achieve specific objectives relating to the invention. A portion of the tube sited within the sealed cavity over the wound may have a structure to enable continued aspiration and evacuation of wound exudates without becoming constricted or blocked even at the higher levels of the negative pressure range envisaged.

It is envisaged that the negative pressure range for the apparatus embodying the present invention may be between about −50 mmHg and −200 mmHg (note that these pressures are relative to normal ambient atmospheric pressure thus, −200 mmHg would be about 560 mmHg in practical terms). Aptly, the pressure range may be between about −75 mmHg and −150 mmHg. Alternatively a pressure range of up to −75 mmHg, up to −80 mmHg or over −80 mmHg can be used. Also aptly a pressure range of below −75 mmHg could be used. Alternatively a pressure range of over −100 mmHg could be used or over −150 mmHg.

The aspiration conduit at its distal end remote from the dressing may be attached to the waste canister at an inlet port or connector. The device containing the means for initiating and sustaining aspiration of the wound/dressing may be situated between the dressing and waste canister, however, in a preferred embodiment of the apparatus embodying the present invention, the device may aspirate the wound/dressing via the canister thus, the waste canister may preferably be sited between the wound/dressing and device.

The aspiration conduit at the waste material canister end may preferably be bonded to the waste canister to prevent inadvertent detachment when being caught on an obstruction, for example.

The canister may be a plastics material moulding or a composite unit comprising a plurality of separate mouldings. The canister may aptly be translucent or transparent in order to visually determine the extent of filling with exudates. However, the canister and device may in some embodiments provide automatic warning of imminent canister full condition and may also provide means for cessation of aspiration when the canister reaches the full condition.

The canister may be provided with filters to prevent the exhaust of liquids and odours therefrom and also to prevent the expulsion of bacteria into the atmosphere. Such filters may comprise a plurality of filters in series. Examples of suitable filters may comprise hydrophobic filters of 0.2 μm pore size, for example, in respect of sealing the canister against bacteria expulsion and 1 μm pore size against liquid expulsion.

Aptly, the filters may be sited at an upper portion of the waste canister in normal use, that is when the apparatus is being used or carried by a patient the filters are in an upper position and separated from the exudate liquid in the waste canister by gravity. Furthermore, such an orientation keeps the waste canister outlet or exhaust exit port remote from the exudate surface.

Aptly the waste canister may be filled with an absorbent gel such as ISOLYSEL (trade mark), for example, as an added safeguard against leakage of the canister when full and being changed and disposed of. Added advantages of a gel matrix within the exudate storing volume of the waste canister are that it prevents excessive movement, such as slopping, of the liquid, minimises bacterial growth and minimises odours.

The waste canister may also be provided with suitable means to prevent leakage thereof both when detached from the device unit and also when the aspiration conduit is detached from the wound site/dressing.

The canister may have suitable means to prevent emptying by a user (without tools or damage to the canister) such that a full or otherwise end-of-life canister may only be disposed of with waste fluid still contained.

The device and waste canister may have mutually complementary means for connecting a device unit to a waste canister whereby the aspiration means in the device unit automatically connects to an evacuation port on the waste canister such that there is a continuous aspiration path from the wound site/dressing to an exhaust port on the device.

In the present invention the aspiration pump means may comprise a diaphragm-type pump which is efficient but tends to have a noisy exhaust caused by the fluid being pumped therethrough and the nature of the manner in which fluid is pumped.

As noted herein the waste canister is provided with suitable filters to prevent the expulsion from the canister of liquid exudate aspirated from the wound. In an embodiment of the present invention the waste canister is sited intermediate the aspirant conduit operably connected to the wound site and the aspirant pump means. Thus whilst the pump means is operating only gaseous fluid exits from the waste canister, liquids and bacteria being retained therein due to the filters as explained herein. Consequently, only gaseous fluids are expelled from the aspiration pump means outlet port and through the silencer system.

The silencing system may comprise a single exhaust conduit portion and a plenum chamber member positioned adjacent an exhaust outlet or further alternatively may itself comprise an exhaust outlet to atmosphere.

Alternatively, and in an embodiment of the present invention, the silencer system may have two primary exhaust conduit portions comprising a first exhaust conduit portion from a pump means outlet port; a plenum chamber member into which the first exhaust conduit portion feeds; and, a second exhaust conduit portion.

The exhaust conduit portion or portions may have predetermined dimensional parameters ducting exhaust fluid to an outlet adjacent a surface of a containing casing.

Such predetermined dimensional parameters of the exhaust conduit portion or portions may relate to length and cross-sectional area of the conduits and may be further related to wavelengths of sound waves passing through the exhaust fluid medium. The predetermined dimensions of the exhaust fluid conduit portions may also reduce the propagation of standing waves in the exhaust conduit portions. The predetermined dimensional parameters may be determined by routine experimentation and may depend inter alia on pump type and pump speed.

Owing to the compact nature of the device unit in which the exhaust system is accommodated, the exhaust conduit portion or portions are necessarily of a convoluted nature in order to connect the various components of the aspiration fluid flow path.

Whilst the exhaust conduit portion or portions may be of predetermined length, that length may be divided into smaller portions so as to accommodate other functions which depend upon a characteristic of the fluid flow therethrough. An example of this may be the provision of a flow meter, intermediate the aspiration pump outlet and the plenum chamber, for example. However, the flow meter may be accommodated in the second exhaust conduit portion if necessary.

The plenum chamber may have a relatively large volume and cross sectional area compared with the exhaust conduit portions. The plenum chamber may also be filled with sound-absorbent material which absorbs most of the sound energy as it is reflected back and forth between the walls of the plenum chamber. Advantageously the sound-absorbent material may also serve the dual purpose of being an odour filter. A suitable material may be CARBOTEC FB3-10.9 supplied by Vitek (trade marks).

In an embodiment of the present invention, the plenum chamber may have an open face which is sealed by an inner face portion of the outer casing structure of the device itself. Thus by disassembling the casing, the sound absorbing odour filtering material in the plenum chamber may be replaced when the device reaches a servicing point, if applicable. Such a structure also serves the additional important advantage of reducing the parts count needed to assemble the device and also lowering cost.

At the exhaust port adjacent the casing there may also be an open pore diffusing member such a foam pad, for example, through which the gaseous exhaust fluid is finally expelled to the atmosphere, the purpose of the diffusing member being to break up as many of the emerging sound waves as possible. However, such a diffuser member is not necessary and the final exhaust outlet may be a simple aperture in the casing.

Aptly, the exhaust port from the fluid path through the apparatus is provided with filter means to prevent offensive odours from being ejected into the atmosphere. As noted above this odour filter may be contained in the plenum chamber.

The silencing system according to the present invention may easily be able to achieve noise levels of less than 50 dBa.

In general terms the device unit comprises an aspirant pump; means for monitoring pressure applied by the aspirant pump; a flowmeter to monitor fluid flow through the aspirant pump; a control system which controls the aspirant pump in response to signals from sensors such as the pressure monitoring means and the flowmeter, for example, and which control system also controls a power management system with regard to an on-board battery pack and the charging thereof and lastly a user interface system whereby various functions of the device such as pressure level set point, for example, may be adjusted (including stopping and starting of the apparatus) by a user. The device unit may contain all of the above features within a single unified casing.

In view of the fact that the device unit contains the majority of the intrinsic equipment cost therein ideally it will also be able to survive impact, tolerate cleaning in order to be reusable by other patients.

In terms of pressure capability the aspiration means may be able to apply a maximum pressure drop of at least −200 mmHg to a wound site/dressing. The apparatus is capable of maintaining a predetermined negative pressure even under conditions where there is a small leak of air into the system and a high exudate flow.

The pressure control system may prevent the minimum pressure achieved from exceeding for example −200 mmHg so as not to cause undue patient discomfort. The pressure required may be set by the user at a number of discreet levels such as −50, −75, −100, −125, −150, −175 mmHg, for example, depending upon the needs of the wound in question and the advice of a clinician. Thus suitable pressure ranges in use may be from −25 to −80 mmHg, or −50 to −76 mmHg, or −50 to −75 mmHg as examples. The control system may also advantageously be able to maintain the set pressure within a tolerance band of +/−10 mmHg of the set point for 95% of the time the apparatus is operating given that leakage and exudation rates are within expected or normal levels.

Aptly, the control system may trigger alarm means such as a flashing light, buzzer or any other suitable means when various abnormal conditions apply such as, for example: pressure outside set value by a large amount due to a gross leak of air into system; duty on the aspiration pump too high due to a relatively smaller leakage of air into the system; pressure differential between wound site and pump is too high due, for example, to a blockage or waste canister full.

The apparatus of the present invention may be provided with a carry case and suitable support means such as a shoulder strap or harness, for example. The carry case may be adapted to conform to the shape of the apparatus comprised in the joined together device and waste canister. In particular, the carry case may be provided with a bottom opening flap to permit the waste canister to be changed without complete removal of the apparatus form the carry case.

The carry case may be provided with an aperture covered by a displaceable flap to enable user access to a keypad for varying the therapy applied by the apparatus.

BRIEF DESCRIPTION OF THE DRAWINGS

In order that the present invention may be more fully understood, examples will now be described by way of illustration only with reference to the accompanying drawings, of which.

DETAILED DESCRIPTION OF SOME EXEMPLIFYING EMBODIMENTS

Figure 1:
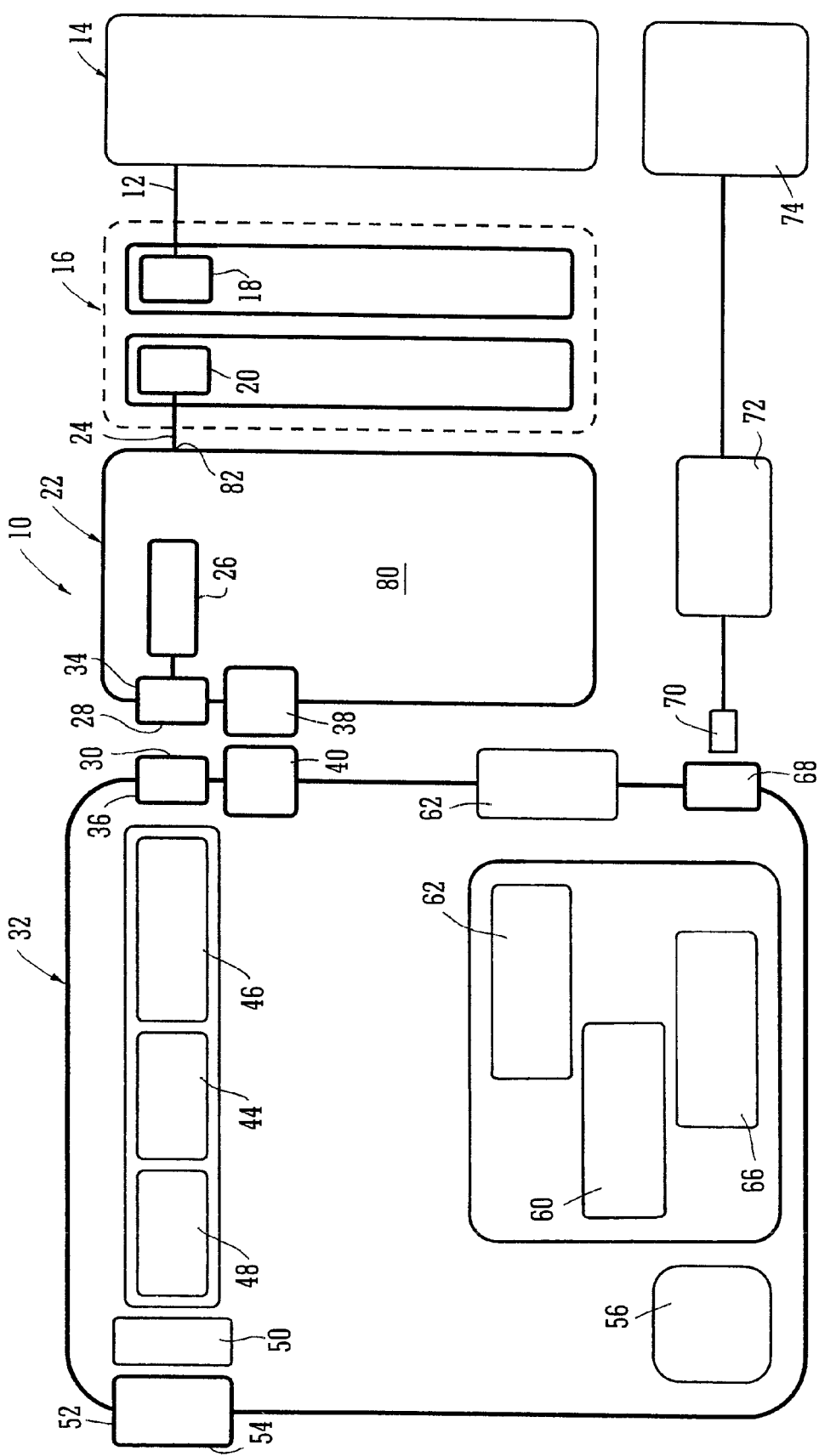
FIG. 1 shows a generalised schematic block diagram showing a general view of an apparatus and the constituent apparatus features thereof.

Referring now to FIGS. 1 to 4 of the drawings and where the same or similar features are denoted by common reference numerals.

FIG. 1 shows a generalised schematic view of an apparatus 10 of a portable topical negative pressure (TNP) system. It will be understood that embodiments of the present invention are generally applicable to use in such a TNP system. Briefly, negative pressure wound therapy assists in the closure and healing of many forms of "hard to heal" wounds by reducing tissue oedema; encouraging blood flow and granular tissue formation; removing excess exudate and may reduce bacterial load (and, therefore, infection). In addition the therapy allows for less disturbance of a wound leading to more rapid healing. The TNP system is detailed further hereinafter but in summary includes a portable body including a canister and a device with the device capable of providing an extended period of continuous therapy within at least a one year life span. The system is connected to a patient via a length of tubing with an end of the tubing operably secured to a wound dressing on the patient.

More particularly, as shown in FIG. 1, the apparatus comprises an aspiration conduit 12 operably and an outer surface thereof at one end sealingly attached to a dressing 14. The dressing 14 will not be further described here other than to say that it is formed in a known manner from well know materials to those skilled in the dressings art to create a sealed cavity over and around a wound to be treated by TNP therapy with the apparatus of the present invention. The aspiration conduit has an in-line connector 16 comprising connector portions 18, 20 intermediate its length between the dressing 14 and a waste canister 22. The aspiration conduit between the connector portion 20 and the canister 22 is denoted by a different reference numeral 24 although the fluid path through conduit portions 12 and 24 to the waste canister is continuous. The connector portions 18, 20 join conduit portions 12, 24 in a leak-free but disconnectable manner. The waste canister 22 is provided with filters 26 which prevent the escape via an exit port 28 of liquid and bacteria from the waste canister. The filters may comprise a 1 μm hydrophobic liquid filter and a 0.2 μm bacteria filter such that all liquid and bacteria is confined to an interior waste collecting volume of the waste canister 22. The exit port 28 of the waste canister 22 mates with an entry/suction port 30 of a device unit 32 by means of mutually sealing connector portions 34, 36 which engage and seal together automatically when the waste canister 22 is attached to the device unit 32, the waste canister 22 and device unit 32 being held together by catch assemblies 38, 40. The device unit 32 comprises an aspirant pump 44, an aspirant pressure monitor 46 and an aspirant flowmeter 48 operably connected together. The aspiration path takes the aspirated fluid which in the case of fluid on the exit side of exit port 28 is gaseous through a silencer system 50 and a final filter 52 having an activated charcoal matrix which ensures that no odours escape with the gas exhausted from the device 32 via an exhaust port 54. The filter 52 material also serves as noise reducing material to enhance the effect of the silencer system 50. The device 32 also contains a battery pack 56 to power the apparatus which battery pack also powers the control system 60 which controls a user interface system 62 controlled via a keypad (not shown) and the aspiration pump 44 via signals from sensors 46, 48. A power management system 66 is also provided which controls power from the battery pack 56, the recharging thereof and the power requirements of the aspirant pump 44 and other electrically operated components. An electrical connector 68 is provided to receive a power input jack 70 from a SELV power supply 72 connected to a mains supply 74 when the user of the apparatus or the apparatus itself is adjacent a convenient mains power socket.

Figure 2:
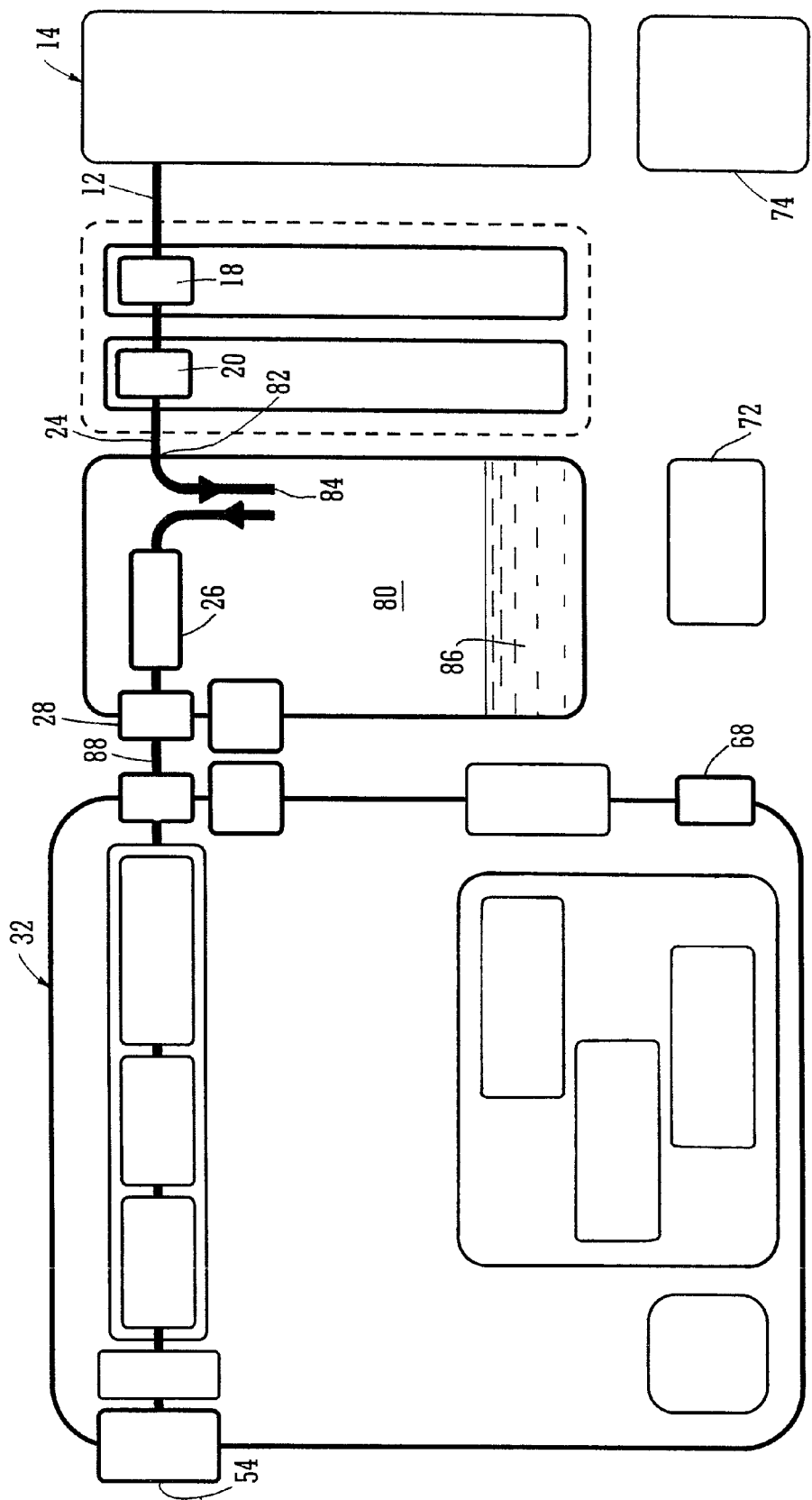
FIG. 2 shows a similar generalised schematic block diagram to FIG. 1 and showing fluid paths therein.

FIG. 2 shows a similar schematic representation to FIG. 1 but shows the fluid paths in more detail. The wound exudate is aspirated from the wound site/dressing 14 via the conduit 12, the two connector portions 18, 20 and the conduit 24 into the waste canister 22. The waste canister 22 comprises a relatively large volume 80 in the region of 500 ml into which exudate from the wound is drawn by the aspiration system at an entry port 82. The fluid 84 drawn into the canister volume 80 is a mixture of both air drawn into the dressing 14 via the semi-permeable adhesive sealing drape (not shown) and liquid 86 in the form of wound exudates. The volume 80 within the canister is also at a lowered pressure and the gaseous element 88 of the aspirated fluids is exhausted from the canister volume 80 via the filters 26 and the waste canister exhaust exit port 28 as bacteria-free gas. From the exit port 28 of the waste canister to the final exhaust port 54 the fluid is gaseous only.

Figure 3:
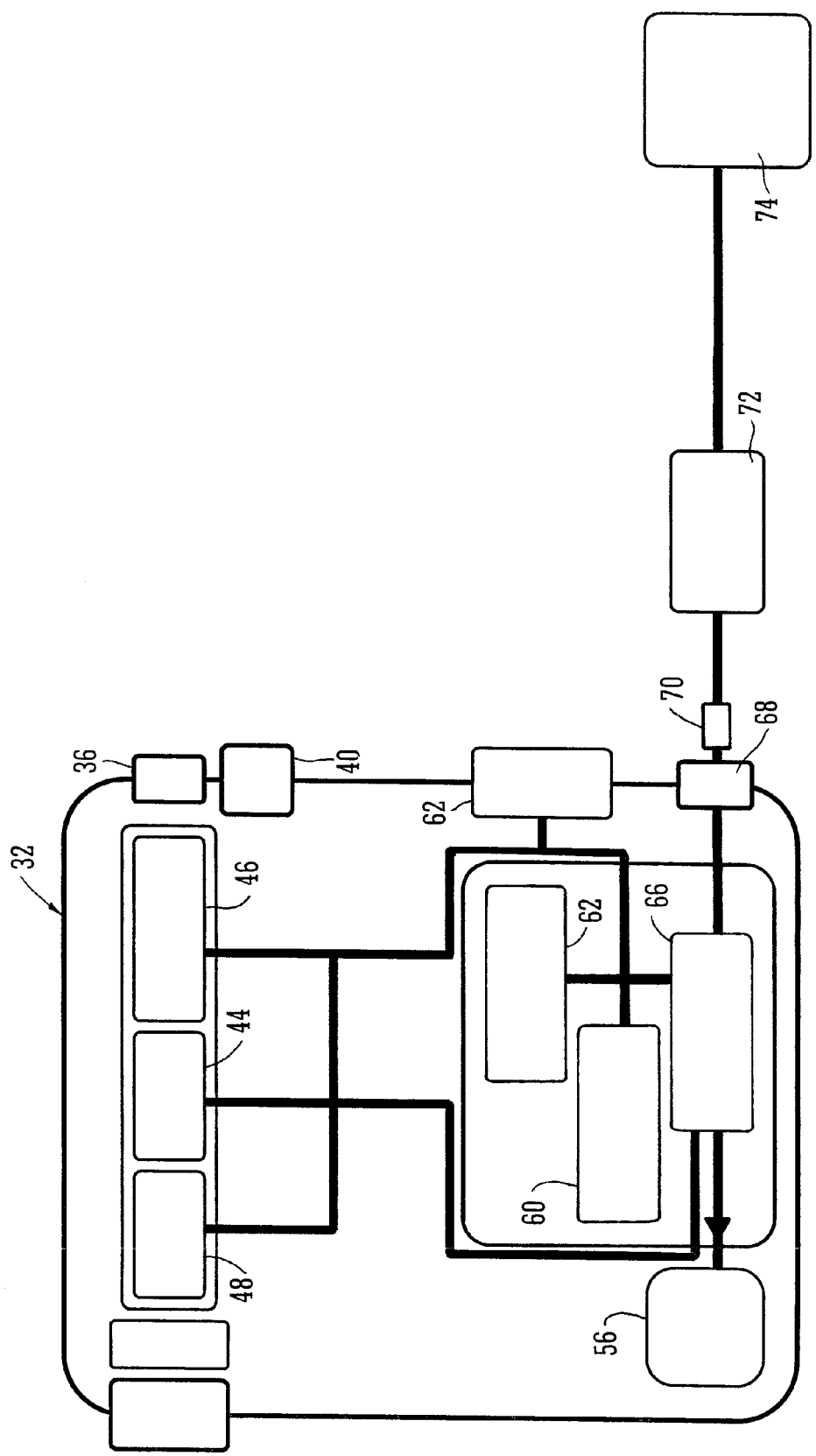
FIG. 3 shows a generalised schematic block diagram similar to FIG. 1 but of a device unit only and showing power paths for the various power consuming/producing features of the apparatus.

FIG. 3 shows a schematic diagram showing only the device portion of the apparatus and the power paths in the device of the apparatus embodying the present invention. Power is provided mainly by the battery pack 56 when the user is outside their home or workplace, for example, however, power may also be provided by an external mains 74 supplied charging unit 72 which when connected to the device 32 by the socket 68 is capable of both operating the device and recharging the battery pack 56 simultaneously. The power management system 66 is included so as to be able to control power of the TNP system. The TNP system is a rechargeable, battery powered system but is capable of being run directly from mains electricity as will be described hereinafter more fully with respect to the further figures. If disconnected from the mains the battery has enough stored charge for approximately 8 hours of use in normal conditions. It will be appreciated that batteries having other associated life times between recharge can be utilised. For example batteries providing less than 8 hours or greater than 8 hours can be used. When connected to the mains the device will run off the mains power and will simultaneously recharge the battery if depleted from portable use. The exact rate of battery recharge will depend on the load on the TNP system. For example, if the wound is very large or there is a significant leak, battery recharge will take longer than if the wound is small and well sealed.

Figure 4:
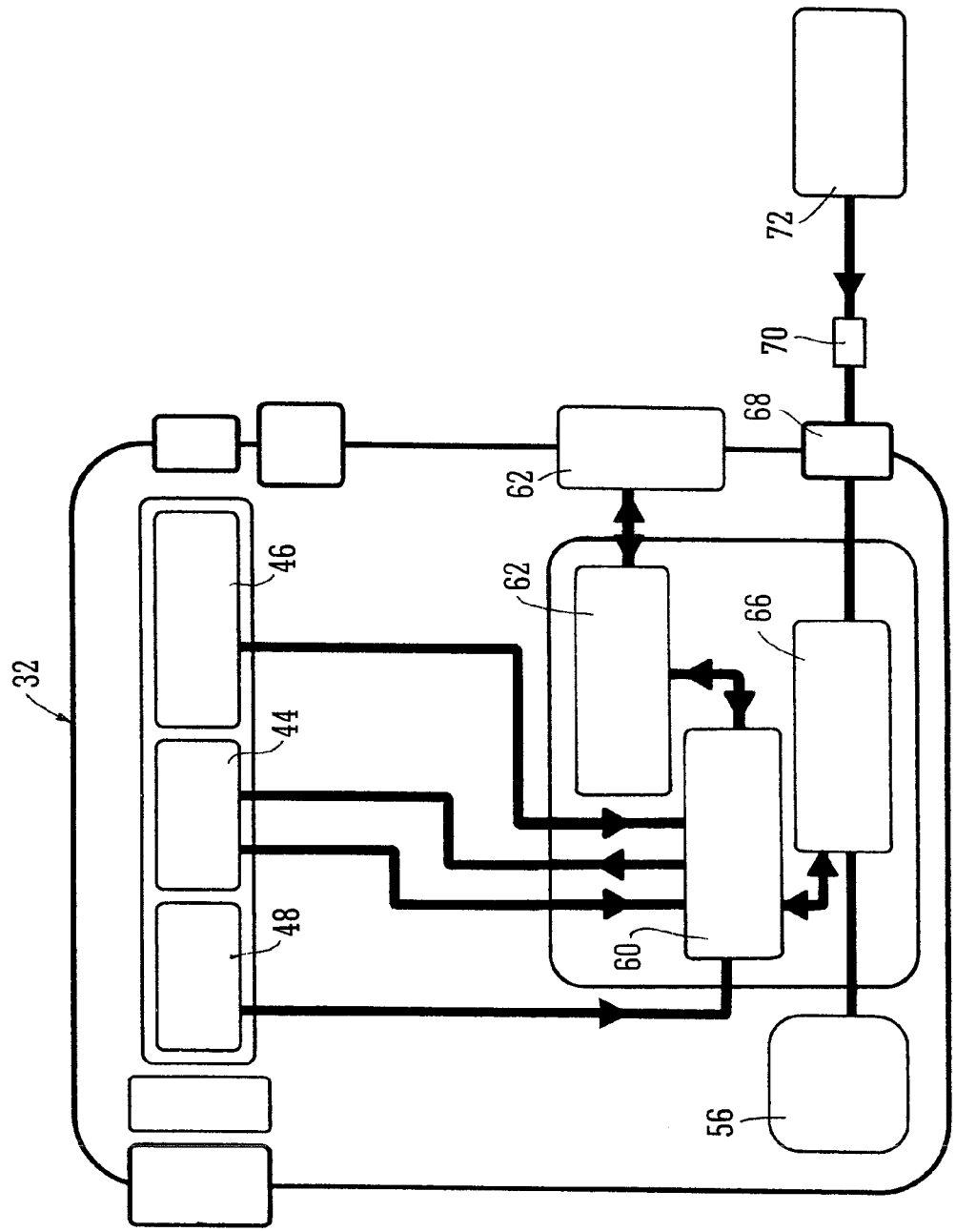
FIG. 4 shows a similar generalised schematic block diagram to FIG. 3 of the device unit and showing control system data paths for controlling the various functions and components of the apparatus.
Figure 5:
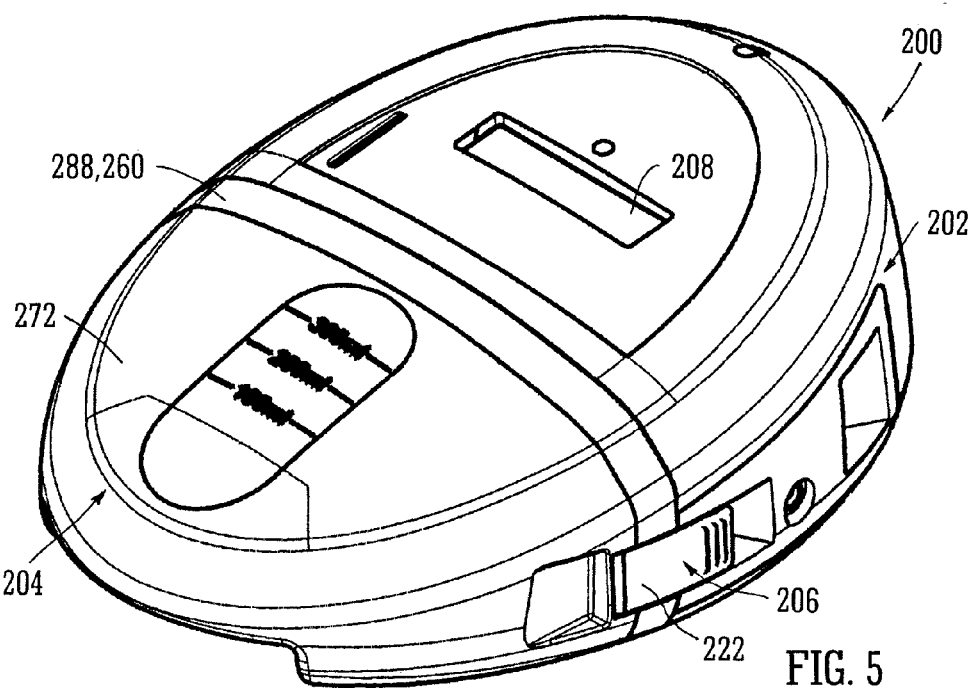
FIG. 5 shows a perspective view of an apparatus.
Figure 6:
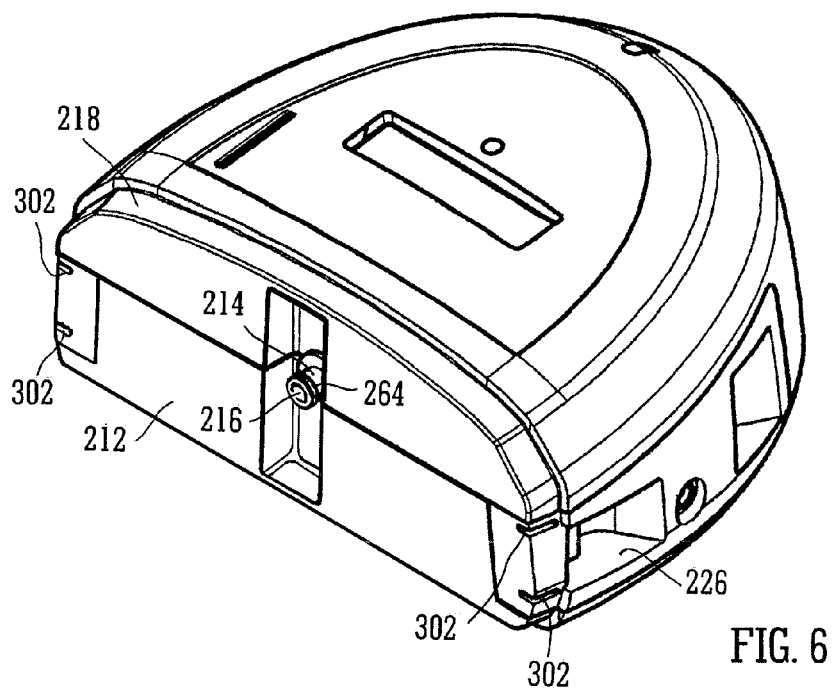
FIG. 6 shows a perspective view of an assembled device unit of the apparatus of FIG. 5.
Figure 7:
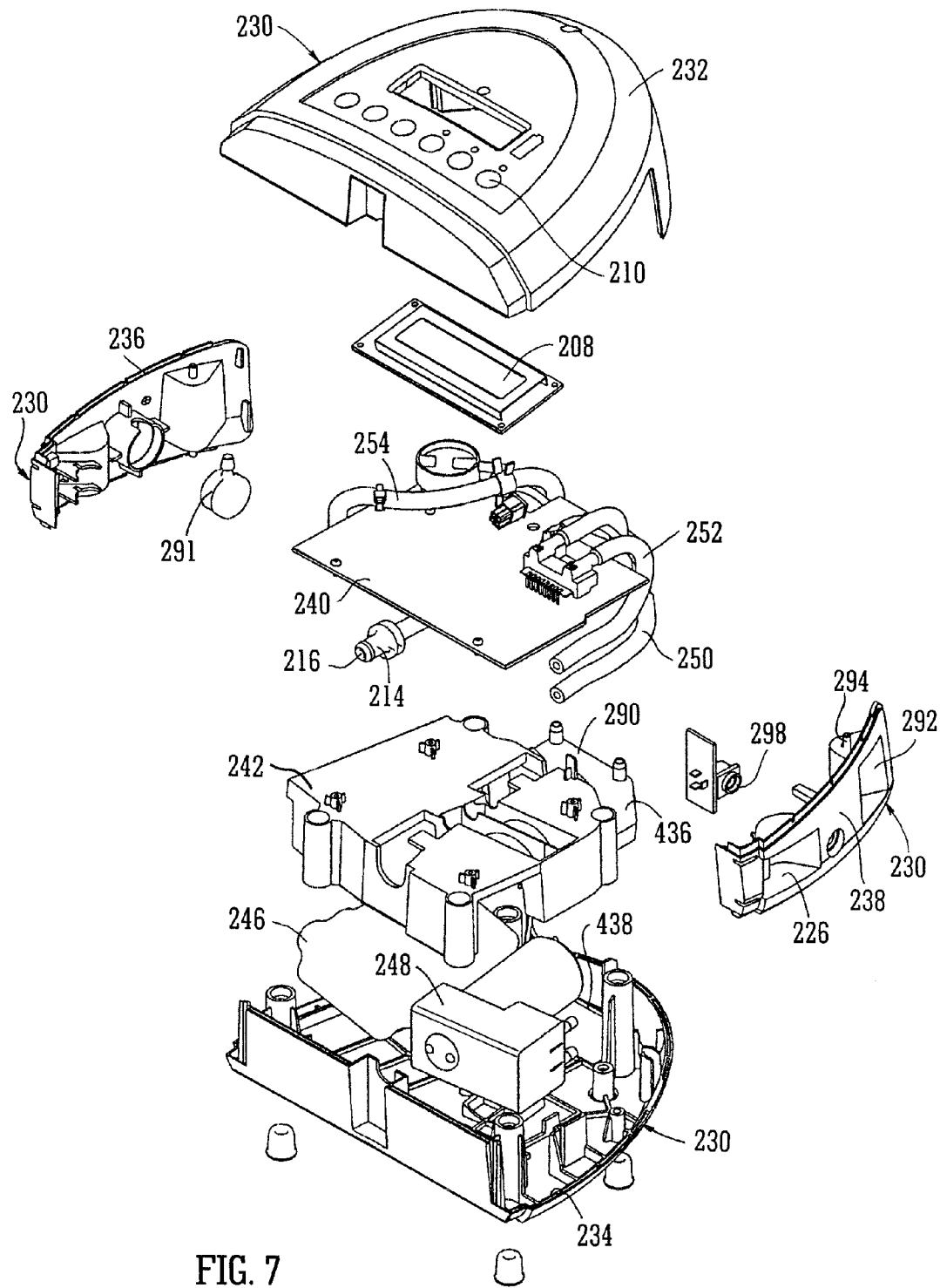
FIG. 7 shows an exploded view of the device unit of FIG. 6.

FIG. 4 shows the device 32 part of the apparatus embodying the present invention and the data paths employed in the control system for control of the aspirant pump and other features of the apparatus. A key purpose of the TNP system is to apply negative pressure wound therapy. This is accomplished via the pressure control system which includes the pump and a pump control system. The pump applies negative pressure; the pressure control system gives feedback on the pressure at the pump head to the control system; the pump control varies the pump speed based on the difference between the target pressure and the actual pressure at the pump head. In order to improve accuracy of pump speed and hence provide smoother and more accurate application of the negative pressure at a wound site, the pump is controlled by an auxiliary control system. The pump is from time to time allowed to "free-wheel" during its duty cycle by turning off the voltage applied to it. The spinning motor causes a "back electro-motive force" or BEMF to be generated. This BEMF can be monitored and can be used to provide an accurate measure of pump speed. The speed can thus be adjusted more accurately than can prior art pump systems.

According to embodiments of the present invention, actual pressure at a wound site is not measured but the difference between a measured pressure (at the pump) and the wound pressure is minimised by the use of large filters and large bore tubes wherever practical. If the pressure control measures that the pressure at the pump head is greater than a target pressure (closer to atmospheric pressure) for a period of time, the device sends an alarm and displays a message alerting the user to a potential problem such as a leak.

In addition to pressure control a separate flow control system can be provided. A flow meter may be positioned after the pump and is used to detect when a canister is full or the tube has become blocked. If the flow falls below a certain threshold, the device sounds an alarm and displays a message alerting a user to the potential blockage or full canister.

Figure 8:
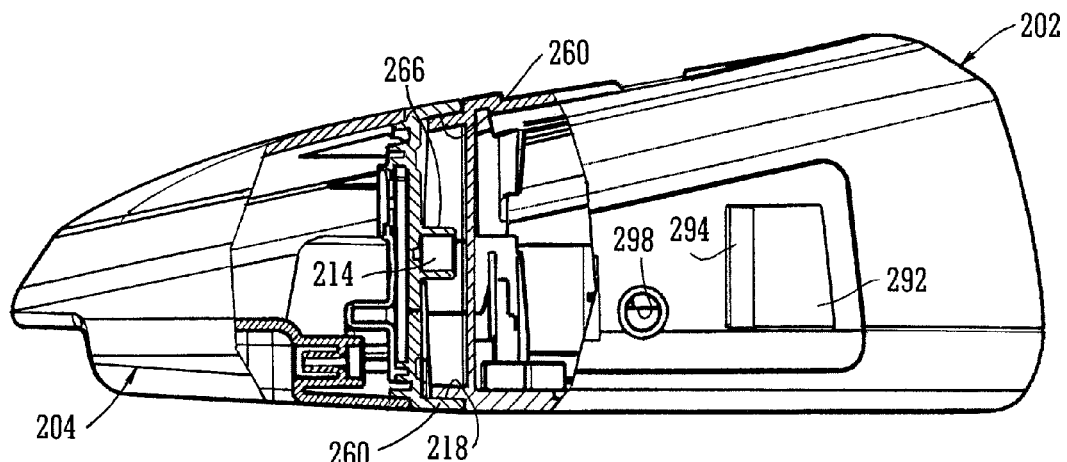
FIG. 8 shows a partially sectioned side elevation view through the interface between a waste canister and device unit of the apparatus.
Figure 9:
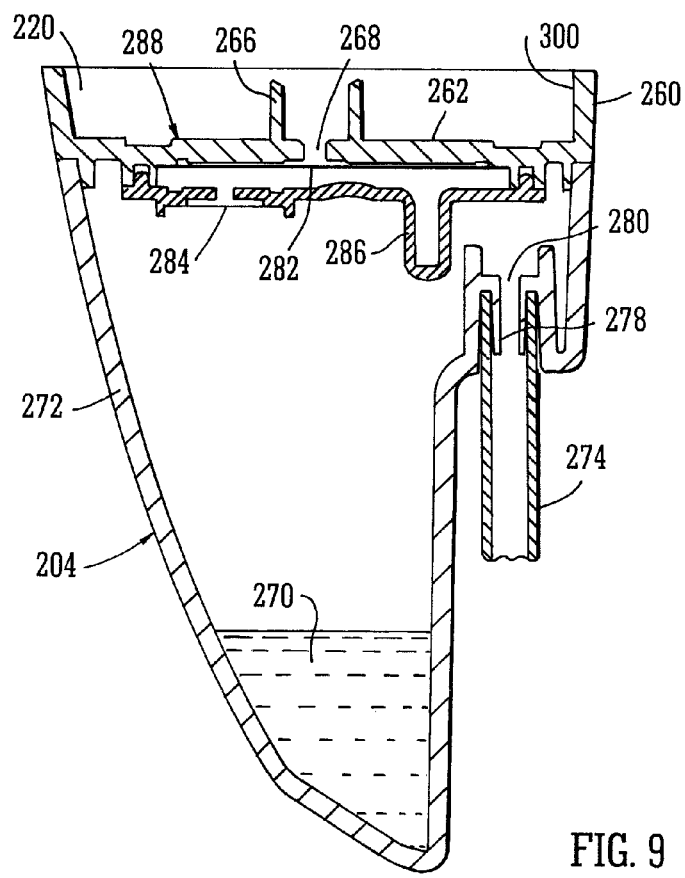
FIG. 9 shows a cross section through a waste canister of the apparatus of FIGS. 5 to 8.
Figure 10:
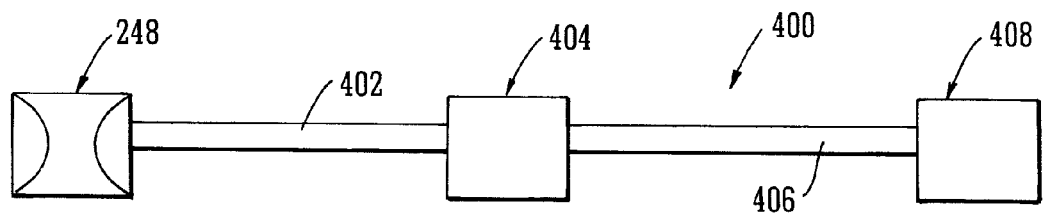
FIG. 10 shows a schematic representation of an exhaust silencer system according to the present invention.
Figure 11:
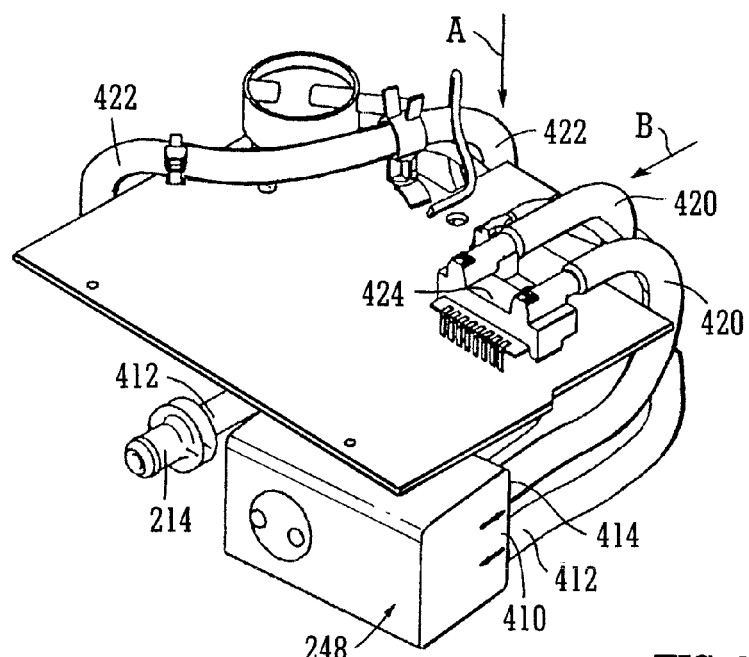
FIG. 11 shows a detail of a preferred embodiment of apparatus for the application TNP therapy and embodying an exhaust silencing system according to the present invention.
Figure 12:
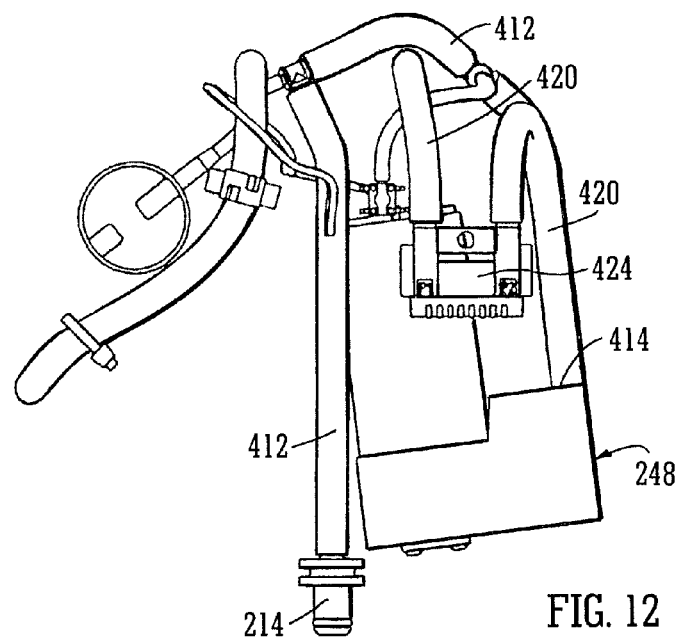
FIG. 12 which is a view of the apparatus of FIG. 11 in the direction of arrow A of FIG. 11 but with chassis plate omitted.
Figure 13:
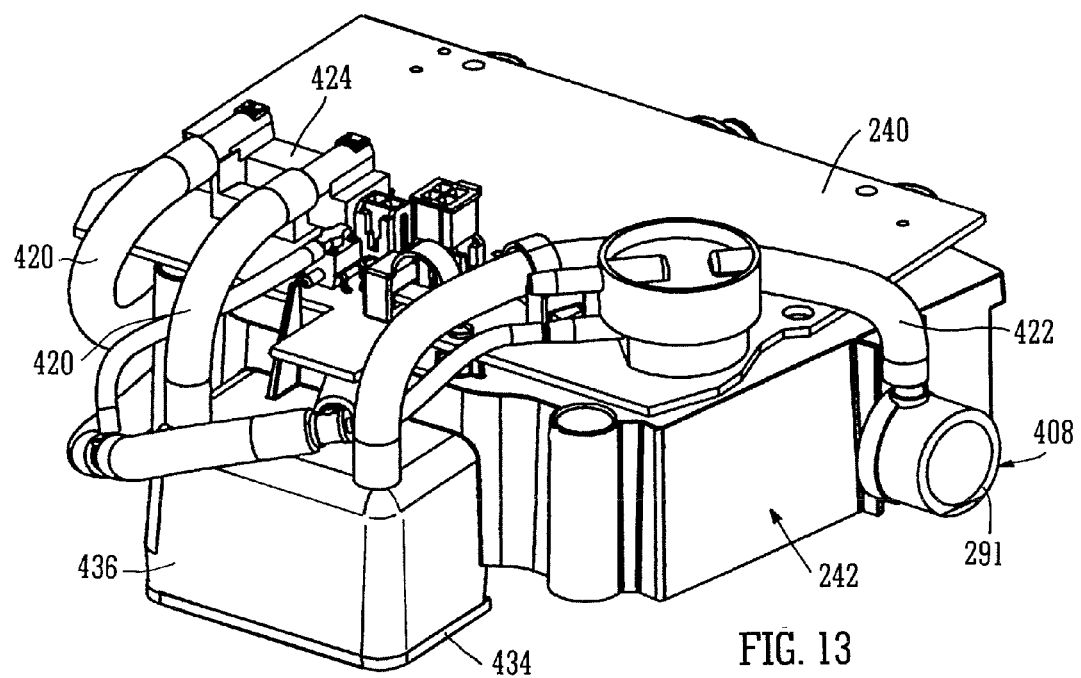
FIG. 13 which is a view of the apparatus of FIG. 11 in the direction of arrow B of FIG. 11.
Figure 14:
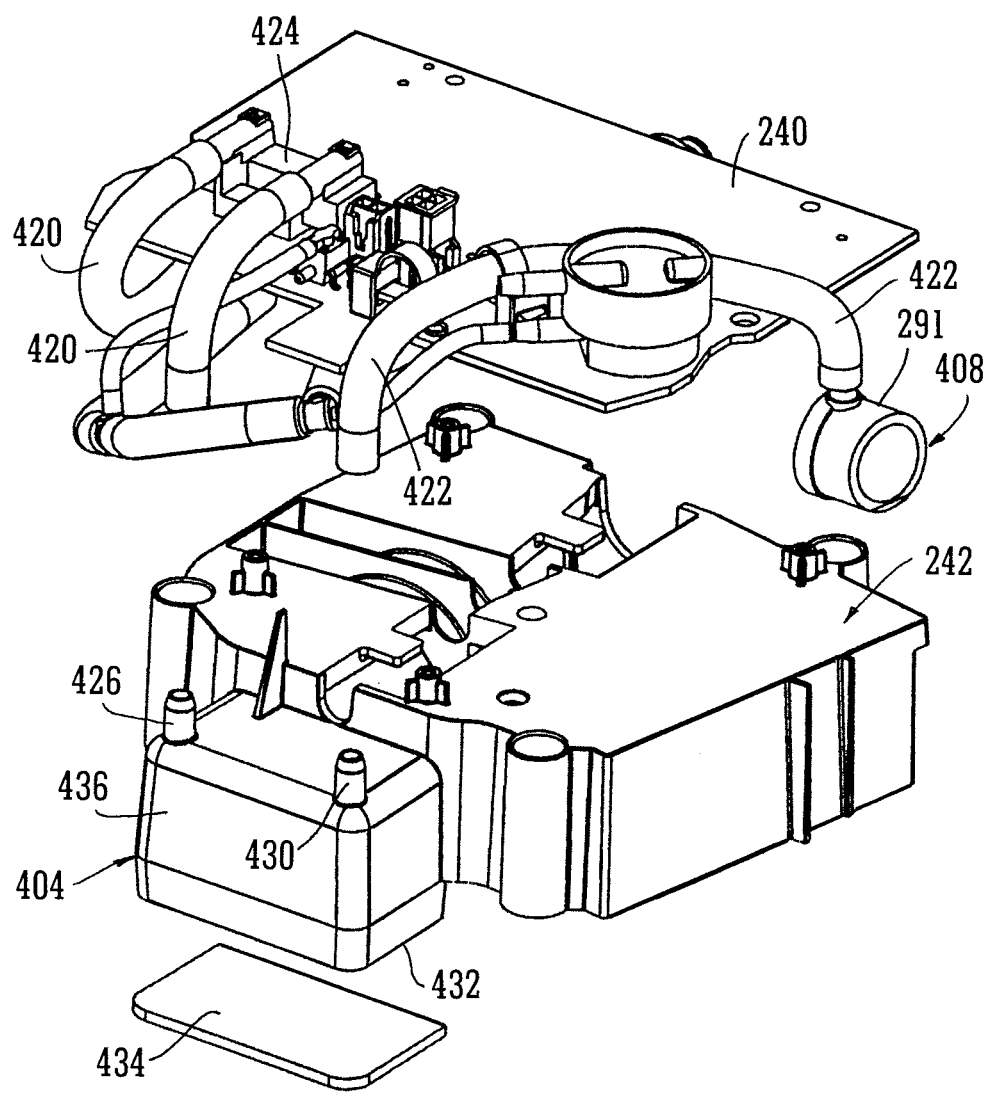
FIG. 14 which shows the apparatus of FIG. 13 exploded.

Referring now to FIGS. 5 to 9 which show various views and cross sections of a preferred embodiment of apparatus 200 embodying the present invention. The preferred embodiment is of generally oval shape in plan and comprises a device unit 202 and a waste canister 204 connected together by catch arrangements 206. The device unit 202 has a liquid crystal display (LCD) 208, which gives text based feedback on the wound therapy being applied, and a membrane keypad 210, the LCD being visible through the membrane of the keypad to enable a user to adjust or set the therapy to be applied to the wound (not shown). The device has a lower, generally transverse face 212 in the centre of which is a spigot 214 which forms the suction/entry port 216 to which the aspiration means (to be described below) are connected within the device unit. The lower edge of the device unit is provided with a rebated peripheral male mating face 218 which engages with a co-operating peripheral female formation 220 on an upper edge of the waste canister 204 (see FIGS. 8 and 9). On each side of the device 202, clips 222 hinged to the canister 204 have an engaging finger (not shown) which co-operates with formations in recesses 226 in the body of the device unit. From FIG. 7 it may be seen that the casing 230 of the device unit is of largely "clamshell" construction comprising front and back mouldings 232, 234, respectively and left-hand and right-hand side inserts 236, 238. Inside the casing 230 is a central chassis 240 which is fastened to an internal moulded structural member 242 and which chassis acts as a mounting for the electrical circuitry and components and also retains the battery pack 246 and aspiration pump unit 248. Various tubing items 250, 252, 254 connect the pump unit 248 and suction/entry port 216 to a final gaseous exhaust via a filter 290. FIG. 8 shows a partially sectioned side elevation of the apparatus 200, the partial section being around the junction between the device unit 202 and the waste canister 204, a cross section of which is shown at FIG. 9. Theses views show the rebated edge 218 of the male formation on the device unit co-operating with the female portion 220 defined by an upstanding flange 260 around the top face 262 of the waste canister 204. When the waste canister is joined to the device unit, the spigot 214 which has an "O" ring seal 264 therearound sealingly engages with a cylindrical tube portion 266 formed around an exhaust/exit port 268 in the waste canister.

The spigot 214 of the device is not rigidly fixed to the device casing but is allowed to "float" or move in its location features in the casing to permit the spigot 214 and seal 264 to move to form the best seal with the bore of the cylindrical tube portion 266 on connection of the waste canister to the device unit. The waste canister 204 in FIG. 9 is shown in an upright orientation much as it would be when worn by a user. Thus, any exudate 270 would be in the bottom of the internal volume of waste receptacle portion 272. An aspiration conduit 274 is permanently affixed to an entry port spigot 278 defining an entry port 280 to receive fluid aspirated from a wound (not shown) via the conduit 274. Filter members 282 comprising a 0.2 µm filter and 284 comprising a 1 µm filter are located by a filter retainer moulding 286 adjacent a top closure member or bulkhead 288 the filter members preventing any liquid or bacteria from being drawn out of the exhaust exit port 268 into the pump and aspiration path through to an exhaust and filter unit 290 which is connected to a casing outlet moulding at 291 via an exhaust tube (not shown) in casing side piece 236. The side pieces 236, 238 are provided with recesses 292 having support pins 294 therein to locate a carrying strap (not shown) for use by the patient. The side pieces 230 and canister 204 are also provided with features which prevent the canister and device from exhibiting a mutual "wobble" when connected together. Ribs (not shown) extending between the canister top closure member 288 and the inner face 300 of the upstanding flange 260 locate in grooves 302 in the device sidewalls when canister and device are connected. The casing 230 also houses all of the electrical equipment and control and power management features, the functioning of which was described briefly with respect to FIGS. 3 and 4 hereinabove. The side piece 238 is provided with a socket member 298 to receive a charging jack from an external mains powered battery charger (both not shown).

Referring now to FIGS. 10 to 14 and where the same or similar features are denoted by common reference numerals.

A silencing system for an aspiration pump 248 of TNP therapy apparatus is denoted generally at 400 and comprises a first exhaust conduit portion 402; a plenum chamber 404; and, a second exhaust conduit portion 406 connected to an exhaust outlet 408. The two exhaust portion conduits 402, 406 are made from silicone rubber such as 60' Shore hardness general purpose coloured silicone tubing and have a length of 156 mm, 128 mm and cross sectional area of 8 sq mm, respectively. These predetermined dimensional parameters are based upon experimentation on a diaphragm pump running at varying speeds (which is employed and controlled by the control system described hereinabove) dictated by the needs of the therapy required. Since the pump may run within a range of speeds, the dimensional parameters are determined by experimentation at average or worst conditions pertaining during operation of the apparatus.

In detail the exhaust silencing system according to a preferred embodiment of the present invention is shown in FIGS. 11 to 14. Gaseous fluid exits from the waste canister 204 via spigot 214 into the gaseous fluid flow path defined in its initial stage to the pump 248 inlet port 410 by conduit 412 attached to the spigot 214. The silencing system 400 is provided between the pump outlet port 414 and the exhaust outlet 408. A first exhaust conduit portion 420 is provided between the pump outlet port 414 and a plenum chamber 404; and, a second exhaust conduit portion 422 between the plenum chamber 404 and the exhaust outlet 408. However, the first exhaust conduit portion 420 is provided with a flow meter 424 intermediate its ends at the pump outlet 414 and an inlet 426 of the plenum chamber 404. The flow meter 424 is provided to fulfil various control functions including determining when the waste canister 204 is full. Since it is necessary that the fluid flow values measured by the flow meter 424 are accurate it is positioned in the first conduit portion 420 rather than the second conduit portion 422 in case the plenum chamber 404 should leak for any reason and cause spurious flow measurements. However, other than this reason, the flow meter 424 could be positioned in the second conduit portion 422. The flow meter 424 is connected electrically to the control system described hereinabove. The second exhaust conduit portion 422 is connected to an outlet 430 of the plenum chamber 404 and the exhaust outlet 408. At the exhaust outlet 408, the second exhaust conduit portion 422 is connected to the moulding 291 which locates in the outer casing side piece 236 described with reference to FIG. 7 hereinabove. The moulding 291 may contain a final diffuser element such as an open-pore foam pad (not shown) to further break up any remaining sound waves which reach the outlet 408, however, such a foam pad may not be employed as the first and second exhaust conduit portions and the plenum chamber are generally sufficient to reduce the exhaust noise level to an acceptably low level. The plenum chamber 404 comprises a rectangular box-like structure 436 having a lower open face 432 and inlet 426 and outlet 430 and is fixed to the moulded structural member 242. A sealing gasket 434 is provided to engage with an outer rim defining the open face 432. When the complete device 230 is assembled, the rear outer case member 234 (see FIG. 7) has an upstanding rectangular rim 438 which both receives the sealing gasket 434 therein and also the rim defining the lower open face 432 of the plenum chamber 404. Thus when the front and rear casing members 232, 234 are fixed together such as by screws (not shown), for example, the sealing gasket 434 is squeezed between the outer casing member 234 and the rim defining the open face 432 to completely seal the plenum chamber 404. Before assembly the internal volume of the plenum chamber box 436 is filled with fibrous or porous sound absorbing material (not shown) which also serves as an odour filter by virtue of being impregnated with a suitable material such as activated charcoal, for example. The sound absorbing and odour filtering material serves to break up sound waves as they bounce back and forth between opposing walls of the box-like structure 436.

The exhaust silencing system of a preferred embodiment as described hereinabove serves to reduce the noise generated by the pump 248 to very low and entirely acceptable levels so that a patient or wearer is not tempted to turn the apparatus off to gain temporary relief from noise irritation.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

The invention claimed is:

1. A topical negative pressure apparatus comprising:
a casing comprising an exterior portion and an interior portion, the interior portion defining a first interior volume;
a pump configured to aspirate fluid from a wound, the pump located in the first interior volume and attached directly to the inner portion of the casing;
a waste canister configured to collect fluid aspirated from the wound, the waste canister not positioned in the first interior volume and configured to be attached to the casing;
a fluid flow path connecting the pump and the waste canister; and
a silencing system in the fluid flow path, the silencing system comprising:
a first exhaust conduit and a second exhaust conduit;
a plenum chamber situated between the first and second exhaust conduits and positioned within the first interior volume, the plenum chamber comprising a housing defining a second interior volume and an outer rim, the second interior volume comprising sound absorbing material; and
a removable cover integrated into the casing, the cover configured to seal the second interior volume by engaging with the outer rim of the plenum chamber in a first position, the cover further configured to provide access to the second interior volume in a second position so that the sound absorbing material can be replaced, the sound absorbing material configured to remain within the first interior volume when the cover is moved from the first position to the second position.

2. The apparatus of claim 1, wherein the silencing system is configured to reduce a pump noise level to 50 dbA or less.

3. The apparatus of claim 1, wherein the plenum chamber comprises an open face, the open face sealed by the casing of the apparatus.

4. The apparatus of claim 1, wherein the first and second exhaust conduits are connected to a flow meter, the flow meter configured to measure a flow through the conduits.

5. The apparatus of claim 4, wherein the flow meter is configured to determine whether the waste canister is full.

6. The apparatus of claim 1, wherein the first exhaust conduit is connected to an outlet of the pump.

7. The apparatus of claim 6, wherein the silencing system is positioned between the outlet and the exhaust port.

8. The apparatus of claim 1, further comprising an exhaust port connected to the second exhaust conduit.

9. The apparatus of claim 1, wherein:
the pump comprises a diaphragm pump; and
the first and second exhaust conduits comprise a tubing.

10. The apparatus of claim 9, wherein the tubing comprises silicone tubing.

11. The apparatus of claim 9, wherein a diameter of the first exhaust conduit is substantially same as a diameter of the second exhaust conduit.

12. The apparatus of claim 11, wherein the first exhaust conduit is longer than the second exhaust conduit.

13. The apparatus of claim 1, wherein the sound absorbing material is further configured to filter wound odor.

14. The apparatus of claim 13, wherein the sound absorbing material comprises activated charcoal.

15. The apparatus of claim 1, wherein the sound absorbing material is configured to absorb standing sound waves.

16. The apparatus of claim 1, wherein the removable cover comprises a sealing gasket configured to seal the second interior volume, the sealing gasket further configured to extend substantially across entire area of the removable cover.

17. The apparatus of claim 16, wherein the sealing gasket is squeezed between the casing and the outer rim of the plenum chamber when the removable cover is in the first position.

18. The apparatus of claim 1, wherein the first and second exhaust conduits are positioned within the first interior volume.

\* \* \* \* \*